US012683006B2

(12) United States Patent
Den Hartog et al.

(10) Patent No.: US 12,683,006 B2
(45) Date of Patent: Jul. 14, 2026

(54) IMAGE ACQUISITION VISUALS FOR AUGMENTED REALITY

(71) Applicant: KONINKLIJKE PHILIPS N.V., Eindhoven (NL)

(72) Inventors: Markus Johannes Harmen Den Hartog, Eindhoven (NL); Javier Olivan Bescos, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 148 days.

(21) Appl. No.: 18/887,177

(22) Filed: Sep. 17, 2024

(65) Prior Publication Data

US 2025/0014712 A1     Jan. 9, 2025

Related U.S. Application Data

(63) Continuation of application No. 17/776,042, filed as application No. PCT/EP2020/081740 on Nov. 11, 2020, now abandoned.

(30) Foreign Application Priority Data

Nov. 15, 2019     (EP) ..................................... 19209345

(51) Int. Cl.
*G16H 20/40*          (2018.01)
*A61B 34/20*          (2016.01)
          (Continued)

(52) U.S. Cl.
CPC ............. *G16H 20/40* (2018.01); *A61B 34/20* (2016.02); *A61B 90/37* (2016.02); *G16H 30/20* (2018.01);
          (Continued)

(58) Field of Classification Search
CPC ..... G06T 19/006; G06T 17/00; G06T 15/503; G06T 19/00; G06T 2207/10016
See application file for complete search history.

(56) References Cited

U.S. PATENT DOCUMENTS 9,303,982 B1 *   4/2016   Ivanchenko ........... G01B 11/22
2013/0205247 A1   8/2013   Erhard
          (Continued)

FOREIGN PATENT DOCUMENTS

WO        2017117517 A1     7/2017
WO        2018060304 A1     4/2018
WO        2019040493 A1     2/2019

*Primary Examiner* — Van N Chow

(57)          ABSTRACT

Various embodiments of the present disclosure encompass a visual image sequence controller (40) for controlling an augmentation of a visual imaging sequence acquisition of an interventional imaging sequence in a rendered augmented view of an image-guided intervention by an augmented reality device (30). The visual imaging sequence acquisition (42) includes, for each interventional image of the interventional imaging sequence (23), an interactive virtual indicator of a sequence number of a corresponding interventional image within the interventional imaging sequence (23) and an imaging parameter of the imaging modality (20) (e.g., a direction, a rotation and/or an angulation of the imaging modality (20)) during an acquisition of the corresponding interventional image by the imaging modality (20). The controller (40) interfaces with the imaging modality (20) and/or a display (24, 31) responsive to a user interaction with at least one of the interactive virtual indicators.

18 Claims, 11 Drawing Sheets

(51) Int. Cl.
    *A61B 90/00*       (2016.01)
    *G16H 30/20*       (2018.01)
    *G16H 40/20*       (2018.01)

(52) U.S. Cl.
    CPC ...... *G16H 40/20* (2018.01); *A61B 2034/2055*
             (2016.02); *A61B 2090/365* (2016.02)

(56)                 References Cited

U.S. PATENT DOCUMENTS

| | | |
|---|---|---|
| 2016/0191887 A1 | 6/2016 | Casas |
| 2017/0186157 A1 | 6/2017 | Boettger |
| 2017/0201708 A1* | 7/2017 | Igarashi ................. H04N 23/63 |
| 2019/0216452 A1* | 7/2019 | Nawana ............... A61B 5/0022 |
| 2019/0231436 A1 | 8/2019 | Panse |
| 2019/0282311 A1 | 9/2019 | Nowlin et al. |
| 2019/0310819 A1 | 10/2019 | Xu |
| 2021/0279952 A1* | 9/2021 | Chen ....................... G06T 17/00 |
| 2022/0374714 A1* | 11/2022 | Nayak ................... G06T 3/4053 |

* cited by examiner

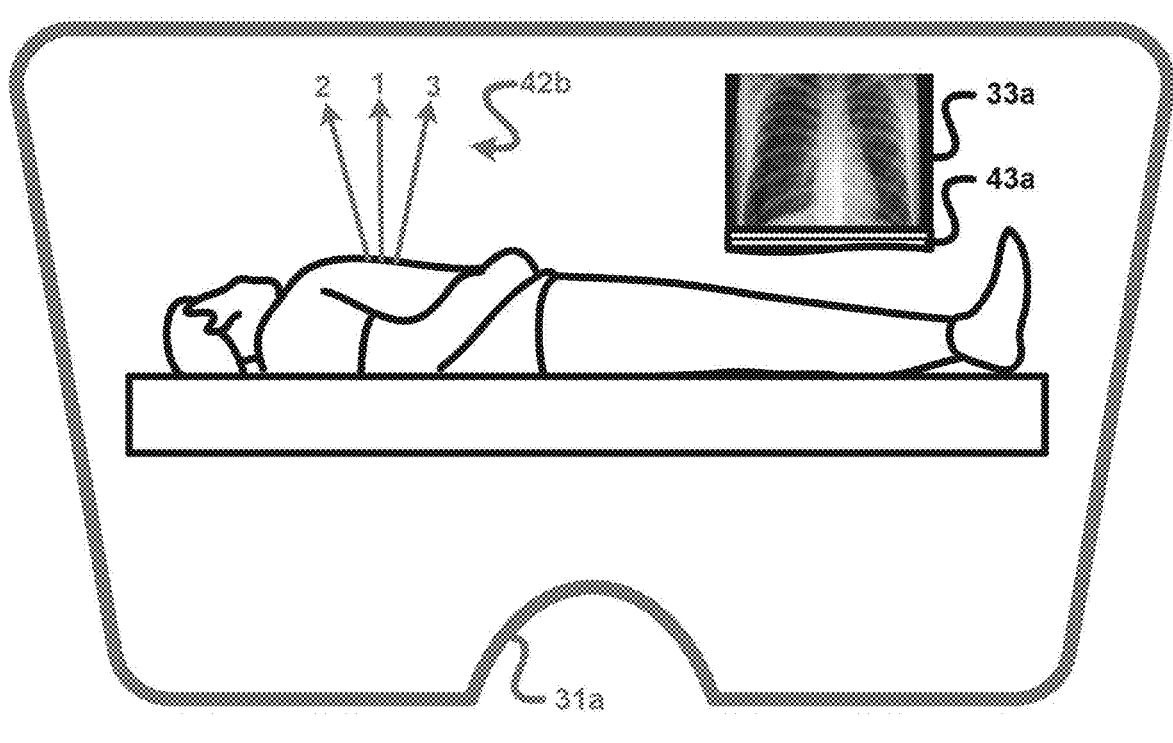
FIG. 4
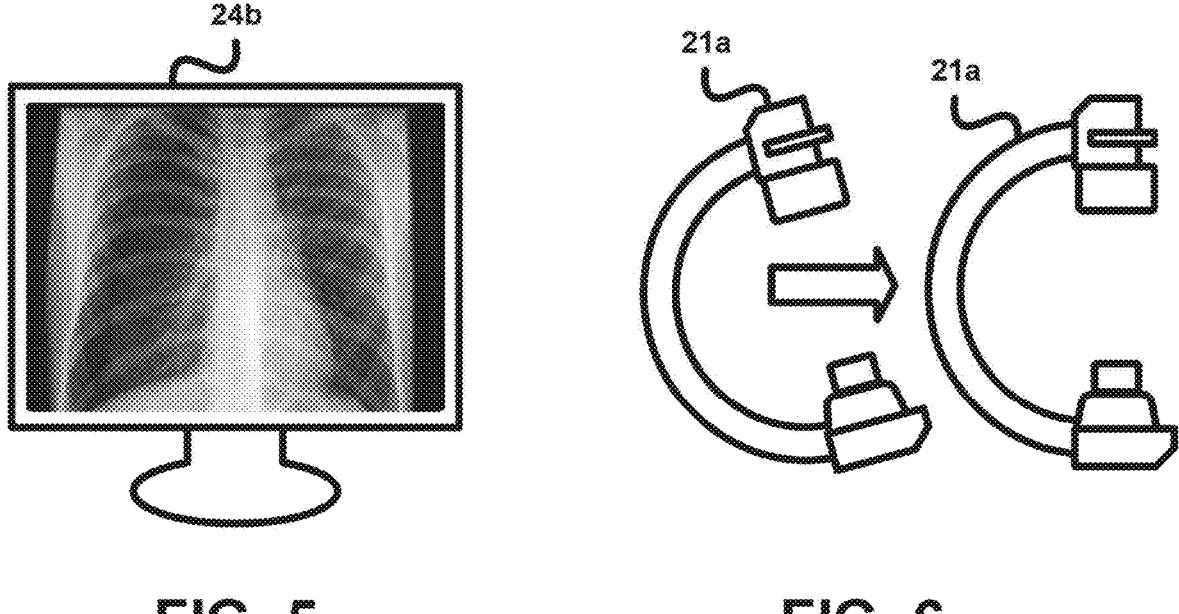
FIG. 5          FIG. 6

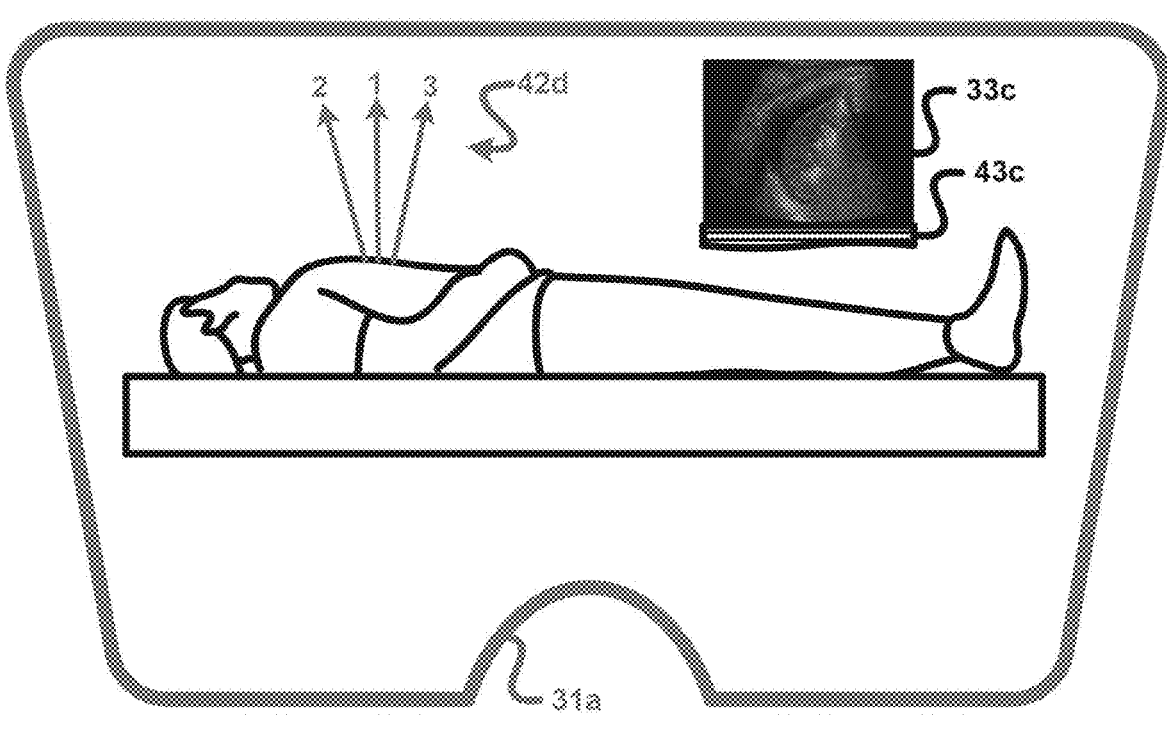
FIG. 11
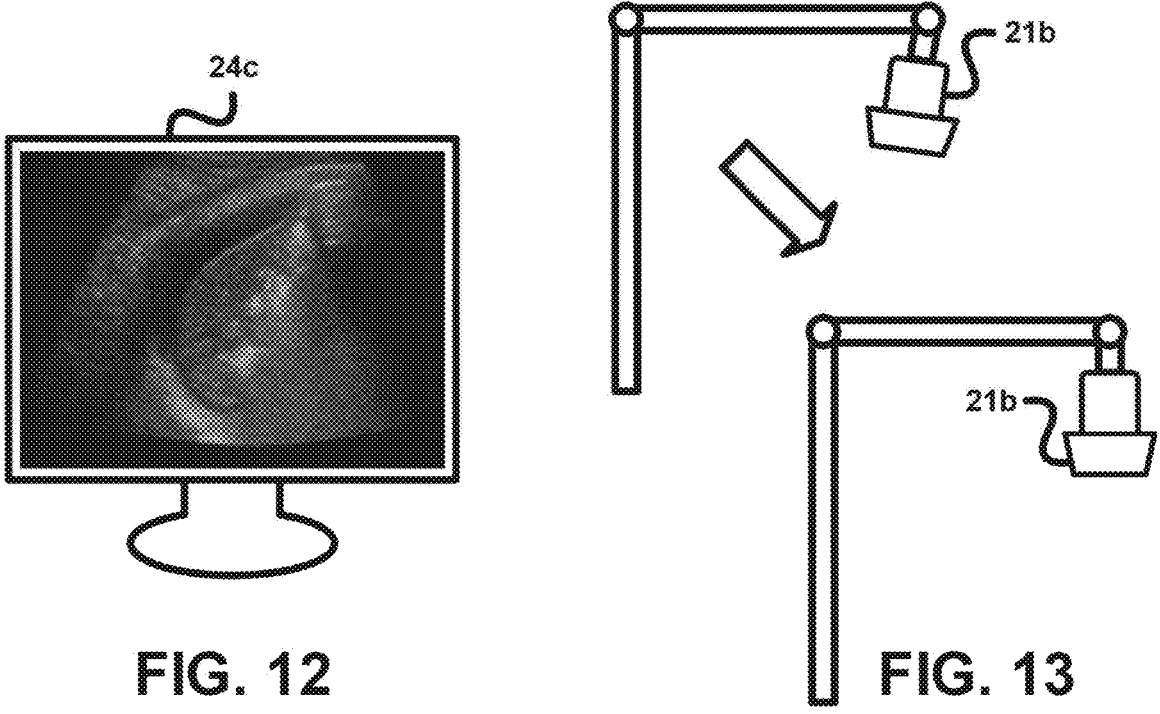
FIG. 12          FIG. 13

IMAGE ACQUISITION VISUALS FOR AUGMENTED REALITY

CROSS-REFERENCE TO RELATED APPLICATIONS

This application is a continuation application of U.S. application Ser. No. 17/776,042, filed on May 11, 2022, which is a U.S. National Phase application under 35 U.S.C. § 371 of International Application No. PCT/EP2020/081740, filed on Nov. 11, 2020, which claims priority to European Application No. 19209345.8, filed on Nov. 15, 2019. These applications are incorporated by reference herein.

FIELD OF THE INVENTION

The present disclosure generally relates to image-guided interventions for a diagnosis and/or a treatment of a three-dimensional (3D) anatomy. The present disclosure specifically relates to an incorporation of augmented reality into image-guided interventions.

BACKGROUND OF THE INVENTION

Two-dimensional (2D) interventional images (e.g., X-ray images, ultrasound images, etc.) are inherently projections of complex three-dimensional (3D) anatomy. To get a sense of a structure of the 3D anatomy during an imaging guided-diagnosis, multiple projections of the 3D anatomy taken from multiple angles of a 2D imaging modality relative to the anatomy are needed. For this reason, in an image-guided intervention, a clinician is provided an opportunity to control a positioning and/or an orientation of the 2D imaging modality to thereby acquire 2D interventional images from a variety of angles (e.g., a clinician manual or programmed control of a C-arm of an X-ray system, a clinician manual or programmed control of a robotic ultrasound probe, etc.).

After a diagnosis of a diseased 3D anatomy via the 2D/3D interventional images, the clinician may decide to treat the diseased 3D anatomy by using interventional tools at the disposal of the clinician. For such an image-guided surgery, the imaging modality is designed to be able to find the optimal viewing angle for visualizing the diseased area as well as positioning and/or an orientating of interventional tools within the diseased area.

In all, during a typical image-guided intervention for diagnosis and/or a treatment of 3D anatomy, a large number of images are taken from a large number of different angles.

More particularly, the clinician frequently needs to access the 2D interventional images taken from previous positions (or even a previous procedure) to validate the diagnosis of the 3D anatomy, to check for anomalies within the 3D anatomy and/or to validate the accuracy of the treatment of the 3D anatomy. Although an imaging modality stores geometry information with the 2D interventional images (e.g., an angulation/rotation of a C-arm, a mechanical scanning of an ultrasound probe, etc.), such geometry information is only available as a linear list. Thus, the clinician needs to make a mental picture of the image-guided intervention to know where an image sequence was taken at which time(s) and at which location(s). Especially for novice users and very long procedures, it is sometimes difficult to get an overview of the whole procedure. So, a clinician typically must navigate through an image sequence linearly, one by one, until they find the 2D interventional image(s) for validating the diagnosis of the 3D anatomy, checking for anomalies within the 3D anatomy and/or validating the accuracy of the treatment of the 3D anatomy.

SUMMARY OF THE INVENTION

It is an object of the present disclosure to provide novel, unique 2D/3D interactive virtual indicators in an augmented reality of an image-guided intervention (e.g., X-ray interventional imaging for diagnosis and/or treatment of 3D anatomy, ultrasound interventional imaging for diagnosis and/or treatment of 3D anatomy, etc.) for graphically displaying, within a physical world, geometric information of an imaging modality associated with a sequential acquisition of 2D/3D interventional images. This advantageously enable interaction of a user, such as a clinician, with a sequence of a portion or an entirety of the image-guided intervention in a natural, yet intuitive way, thereby improving workflows, decision speed and diagnosis and/or treatment quality by enabling the clinician to ascertain an overview of a diagnostic phase and/or a treatment phase of the image-guided intervention.

The present disclosure may be embodied as (1) a visual image sequence controller, (2) an augmented reality device incorporating a visual image sequence controller of the present disclosure, (3) an imaging modality incorporating a visual image sequence controller of the present disclosure, (4) an auxiliary intervention device incorporating a visual image sequence controller of the present disclosure, (5) an augmented image-guided intervention system incorporating an augmented reality device of the present disclosure, an imaging modality of the present disclosure and/or an auxiliary intervention device of the present disclosure, (6) an augmented image-guided intervention method utilizing a visual image sequence controller of the present disclosure; and (7) a visual image sequencing method of the present disclosure.

Various visual image sequence controller embodiments of the present disclosure encompass a visual image sequence controller includes a non-transitory machine-readable storage medium encoded with instructions for execution by one or more processors to control an augmentation of a visual imaging sequence acquisition of an interventional imaging sequence (live or recorded) in a rendered augmented view of an image-guided intervention by an augmented reality device. The non-transitory machine-readable storage medium includes instructions to (1) access geometric information of an imaging modality associated with an acquisition of an interventional imaging sequence of interventional images by the imaging modality during the image-guided intervention, (2) generate a visual imaging sequence acquisition of the interventional imaging sequence including, for each interventional image of the interventional imaging sequence, an interactive virtual indicator of a sequence number of a corresponding interventional image within the interventional imaging sequence and of an imaging parameter of the imaging modality during an acquisition of the corresponding interventional image by the imaging modality, (3) augment the view of the image-guided intervention by the augmented reality device with the interactive virtual indicators as virtual objects indicative of the acquisition of the interventional imaging sequence of interventional images by the imaging modality during the image-guided intervention, and (4) interface with the at least one of the imaging modality and a display responsive to a user interaction with at least one of the interactive virtual indicators. Such imaging parameter can be any information indicative of the geometry (such as direction, rotation or angulation) or status of one or more components of the imaging modality (e.g. a C-arm, an ultrasound probe, etc.) during the acquisition of the interventional image.

Various augmented reality device embodiments of the present disclosure encompass an augmented reality device employing an augmented reality display for viewing an image-guided intervention (live or recorded) and further employing a visual image sequence controller for controlling an augmentation of a visual imaging sequence acquisition of an interventional imaging sequence in the rendered augmented view of the image-guided intervention by the augmented reality device. The visual image sequence controller is configured to (1) access geometric information of an imaging modality associated with an acquisition of an interventional imaging sequence of interventional images by the imaging modality during the image-guided intervention, (2) generate a visual imaging sequence acquisition of the interventional imaging sequence including, for each interventional image of the interventional imaging sequence, an interactive virtual indicator of a sequence number of a corresponding interventional image within the interventional imaging sequence and of an imaging parameter of the imaging modality during an acquisition of the corresponding interventional image by the imaging modality, (3) augment the view of the image-guided intervention by the augmented reality device with the interactive virtual indicators as virtual objects indicative of the acquisition of the interventional imaging sequence of interventional images by the imaging modality during the image-guided intervention, and (4) interface with the at least one of the imaging modality and a display responsive to a user interaction with at least one of the interactive virtual indicators. Such imaging parameter can be any information indicative of the geometry (such as direction, rotation or angulation) or status of one or more components of the imaging modality (e.g. a C-arm, an ultrasound probe, etc.) during the acquisition of the interventional image.

Various imaging modality embodiments of the present disclosure encompass an imaging modality employing an imaging device for generating an interventional imaging sequence of an image-guided intervention, an imaging controller for controlling a generation of the interventional imaging sequence by the imaging device, and further employing a visual image sequence controller for controlling an augmentation of a visual imaging sequence acquisition of the interventional imaging sequence in a rendered augmented view of the image-guided intervention by an augmented reality device. The visual image sequence controller is configured to (1) access geometric information of an imaging modality associated with an acquisition of an interventional imaging sequence of interventional images by the imaging modality during the image-guided intervention, (2) generate a visual imaging sequence acquisition of the interventional imaging sequence including, for each interventional image of the interventional imaging sequence, an interactive virtual indicator of a sequence number of a corresponding interventional image within the interventional imaging sequence and of an imaging parameter of the imaging modality during an acquisition of the corresponding interventional image by the imaging modality, (3) augment the view of the image-guided intervention by the augmented reality device with the interactive virtual indicators as virtual objects indicative of the acquisition of the interventional imaging sequence of interventional images by the imaging modality during the image-guided intervention, and (4) interface with the at least one of the imaging modality and a display responsive to a user interaction with at least one of the interactive virtual indicators. Such imaging parameter can be any information indicative of the geometry (such as direction, rotation or angulation) or status of one or more components of the imaging modality (e.g. a C-arm, an ultrasound probe, etc.) during the acquisition of the interventional image.

Various auxiliary intervention device embodiments of the present disclosure encompass an auxiliary intervention device operable to communicate with an augmented reality device and an imaging modality. The auxiliary intervention further employs a visual image sequence controller for, in communication with the augmented reality device and the imaging modality, controlling an augmentation of a visual imaging sequence acquisition of an interventional imaging sequence in a rendered augmented view of an image-guided intervention by the augmented reality device. The visual image sequence controller is configured to (1) access geometric information of an imaging modality associated with an acquisition of an interventional imaging sequence of interventional images by the imaging modality during the image-guided intervention, (2) generate a visual imaging sequence acquisition of the interventional imaging sequence including, for each interventional image of the interventional imaging sequence, an interactive virtual indicator of a sequence number of a corresponding interventional image within the interventional imaging sequence and of an imaging parameter of the imaging modality during an acquisition of the corresponding interventional image by the imaging modality, (3) augment the view of the image-guided intervention by the augmented reality device with the interactive virtual indicators as virtual objects indicative of the acquisition of the interventional imaging sequence of interventional images by the imaging modality during the image-guided intervention, and (4) interface with the at least one of the imaging modality and a display responsive to a user interaction with at least one of the interactive virtual indicators. Such imaging parameter can be any information indicative of the geometry (such as direction, rotation or angulation) or status of one or more components of the imaging modality (e.g. a C-arm, an ultrasound probe, etc.) during the acquisition of the interventional image.

Various augmented image-guided intervention system embodiments of the present disclosure encompass an augmented image-guided intervention system employing an augmented reality device including an augmented reality display for viewing an image-guided intervention and further employing a visual image sequence controller for controlling an augmentation of a visual imaging sequence acquisition of an interventional imaging sequence in the rendered augmented view of the image-guided intervention by the augmented reality device. The visual image sequence controller is configured to (1) access geometric information of an imaging modality associated with an acquisition of an interventional imaging sequence of interventional images by the imaging modality during the image-guided intervention, (2) generate a visual imaging sequence acquisition of the interventional imaging sequence including, for each interventional image of the interventional imaging sequence, an interactive virtual indicator of a sequence number of a corresponding interventional image within the interventional imaging sequence and of an imaging parameter of the imaging modality during an acquisition of the corresponding interventional image by the imaging modality, (3) augment the view of the image-guided intervention by the augmented reality device with the interactive virtual indicators as virtual objects indicative of the acquisition of the interventional imaging sequence of interventional images by the imaging modality during the image-guided intervention, and (4) interface with the at least one of the imaging modality and a display responsive to a user interaction with at least one of the interactive virtual indicators. The visual image sequence controller is installable, or is installed within the augmented reality device, the imaging modality or an auxiliary intervention device.

Various augmented image-guided intervention method embodiments of the present disclosure encompass an augmented image-guided intervention method involving an augmented reality device rendering an augmented view of an image-guided intervention and further involving a visual image sequence controller controlling an augmentation of a visual imaging sequence acquisition of an interventional imaging sequence in the rendered augmented view of the image-guided intervention by the augmented reality device. In operation, the visual image sequence controller (1) accesses geometric information of an imaging modality associated with an acquisition of an interventional imaging sequence of interventional images by the imaging modality during the image-guided intervention, (2) generates a visual imaging sequence acquisition of the interventional imaging sequence including, for each interventional image of the interventional imaging sequence, an interactive virtual indicator of a sequence number of a corresponding interventional image within the interventional imaging sequence and of an imaging parameter of the imaging modality during an acquisition of the corresponding interventional image by the imaging modality, (3) augments the view of the image-guided intervention by the augmented reality device with the interactive virtual indicators as virtual objects indicative of the acquisition of the interventional imaging sequence of interventional images by the imaging modality during the image-guided intervention, and (4) interfaces with the at least one of the imaging modality and a display responsive to a user interaction with at least one of the interactive virtual indicators. Such imaging parameter can be any information indicative of the geometry (such as direction, rotation or angulation) or status of one or more components of the imaging modality (e.g. a C-arm, an ultrasound probe, etc.) during the acquisition of the interventional image.

Various visual image sequencing method embodiments of the present disclosure encompass visual image sequencing method involving a visual image sequence controller utilizing a linear listing of interventional images to generate an interactive virtual indicator for each interventional image of a visual imaging sequence acquisition by an imaging modality. Each interactive virtual indicator indicates a sequence number of a corresponding interventional image within the interventional imaging sequence and an imaging parameter of the imaging modality during an acquisition of the corresponding interventional image. The visual image sequencing method further involves the visual image sequence controller controlling an augmentation of augmented view of the image-guided intervention with the generated interactive virtual indicators as virtual objects indicative of the acquisition of the interventional imaging sequence of interventional images by the imaging modality during the image-guided intervention.

The foregoing embodiments and other embodiments of the present disclosure as well as various structures and advantages of the present disclosure will become further apparent from the following detailed description of various embodiments of the present disclosure read in conjunction with the accompanying drawings. The detailed description and drawings are merely illustrative of the present disclosure rather than limiting, the scope of the present disclosure being defined by the appended claims and equivalents thereof.

BRIEF DESCRIPTION OF THE DRAWINGS

The present disclosure will present in detail the following description of exemplary embodiments with reference to the following Figures wherein:

FIG. 4 illustrates an augmented reality of the interventional X-ray imaging of FIGS. 3A-3C in accordance with the present disclosure;

FIG. 5 illustrates an X-ray image display of the interventional X-ray imaging of FIGS. 3A-3C in accordance with the present disclosure;

FIG. 6 illustrates a reorientation of an X-ray modality in accordance with the present disclosure;

FIG. 11 illustrates an augmented reality of the interventional ultrasound imaging of FIGS. 10A-10C in accordance with the present disclosure;

FIG. 12 illustrates an ultrasound image display of the interventional ultrasound imaging of FIGS. 10A-10C in accordance with the present disclosure;

FIG. 13 illustrates a reorientation of an ultrasound modality in accordance with the present disclosure;

DETAILED DESCRIPTION OF THE PREFERRED EMBODIMENTS

The present disclosure is applicable to image-guided intervention implementing minimally-invasive imaging to diagnose and/or treat anatomical diseases (e.g., X-ray interventional imaging of organs, ultrasound interventional imaging of organs, etc.).

The present disclosure improves upon the prior art of image-guided intervention by providing unique embodiments of 2D/3D interactive virtual indicators in an augmented reality of an image-guided intervention (live or recorded) for graphically displaying, within a physical world, geometric information of an imaging modality associated with a sequential acquisition of 2D/3D interventional images to thereby illustrate a sequence of a portion or an entirety of the image-guided intervention to a clinician in a natural way.

Figures 1, 2:
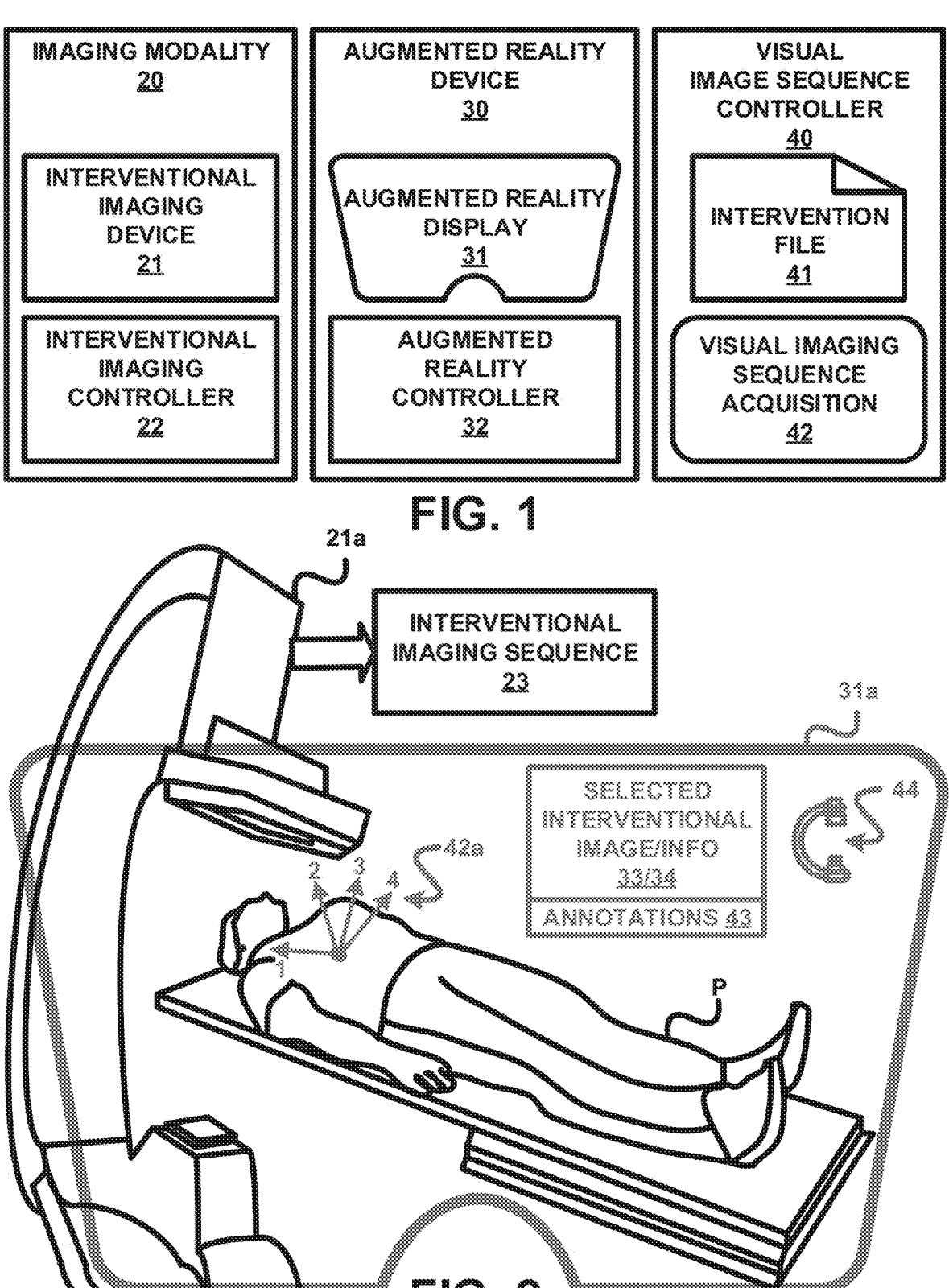
FIG. 1 illustrates an exemplary embodiment of an augmented image-guided intervention system in accordance with the present disclosure.
FIG. 2 illustrates an exemplary embodiment of augmented image-guided intervention in accordance with the present disclosure.

To facilitate an understanding of the present disclosure, the following description of FIGS. 1 and 2 teaches respective exemplary embodiments of an augmented image-guided intervention system and an augmented image-guided intervention method in accordance with the present disclosure. From the description of FIGS. 1 and 2, those having ordinary skill in the art of the present disclosure will appreciate how to apply the present disclosure to make and use additional embodiments of augmented image-guided intervention system of the present disclosure and augmented image-guided intervention method of the present disclosure.

Referring to FIG. 1, an exemplary augmented image-guided intervention system of the present disclosure employs an imaging modality 20, an augmented reality device 30 and a visual image sequence controller 40.

For purposes of describing and claiming the present disclosure, the term "imaging modality" encompasses all systems, as known in the art of the present disclosure and hereinafter conceived, for implementing an image-guided intervention procedure by directing energy (e.g., X-ray beams, ultrasound, radio waves, magnetic fields, light, electrons, lasers, and radionuclides) into an anatomy for purposes of generating images of the anatomy (e.g., biological tissues and bone). Examples of an imaging modality include, but are not limited to, interventional X-ray imaging systems and interventional ultrasound systems.

In practice, imaging modality 20 includes an interventional imaging controller 22 for controlling an activation/deactivation of an interventional imaging device 21 (e.g., an X-ray C-arm, an ultrasound probe, etc.) to systematically direct energy into an anatomy via operator-generated commands and/or image guided procedural-generated commands for purposes of generating images of the anatomy as known in the art of the present disclosure.

For purposes of describing and claiming the present disclosure, the term "augmented reality device" encompasses all devices, as known in the art of the present disclosure and hereinafter conceived, for implementing an interactive experience of overlaying virtual object(s) in a physical world of image-guided intervention based on an accurate spatial registration of the augmented reality device to the physical world of image-guided intervention that facilitates a consistent positioning and orienting of the virtual object(s) in the real-world image-guided intervention. Examples of an augmented reality device include, but are not limited to, Microsoft Hololens®, Microsoft HoloLens® v2, DAQRI Smart Glasses®, Magic Leap®, Vusix Blade® and Meta2®.

In practice, augmented reality device 30 includes an augmented reality controller 32 for controlling augmented reality display 31 to display virtual object(s) in a physical world of image-guided intervention based on an accurate spatial registration of augmented reality display 31 to imaging modality 20 and/or the subject anatomy that facilitates a consistent positioning and orienting of the virtual object(s) to the subject anatomy and an operator-interaction with the virtual object(s).

For purposes of describing and claiming the present disclosure, the term "visual image sequence controller" encompasses all structural configurations, as understood in the art of the present disclosure and as exemplary described in the present disclosure, of a main circuit board or an integrated circuit for controlling an application of various principles of the present disclosure for an augmentation of a visual imaging sequence acquisition of an interventional imaging sequence in a rendered augmented view of the image-guided intervention by an augmented reality device as exemplary described in the present disclosure. The structural configuration of the controller may include, but is not limited to, processor(s), computer-usable/computer readable storage medium(s), an operating system, application module(s), peripheral device controller(s), slot(s) and port(s).

For purposes of describing and claiming the present disclosure, the term "application module" broadly encompasses an application incorporated within or accessible by a controller consisting of an electronic circuit (e.g., electronic components and/or hardware) and/or an executable program (e.g., executable software stored on non-transitory computer readable medium(s) and/or firmware) for executing a specific application associated with implementing an augmentation of a visual imaging sequence acquisition of an interventional imaging sequence in a rendered augmented view of the image-guided intervention by the augmented reality device In practice, as exemplary described in the present disclosure, visual image sequence controller 40 access an intervention file 41 informative of geometric information of imaging modality 20 associated with an acquisition of 2D/3D interventional images to thereby control an augmentation of a visual imaging sequence acquisition of an interventional imaging sequence by imaging modality 20 in a rendered augmented view of the image-guided intervention by augmented reality device 30. The visual imaging sequence acquisition includes, for each interventional image of the interventional imaging sequence, an interactive virtual indicator of a sequence number and an imaging direction during an acquisition of the interventional image by imaging modality 20.

More particularly, augmented reality controller 32 facilitates a rendering of computer generated content as overlay on an augmented view of an image-guided intervention. When a pose of the eyes are known by augmented reality controller 32, the visual imaging acquisition 42 can be rendered such that it appears to be part of the image-guided intervention. For this to happen, augmented reality device 30 and the subject anatomy need to be accurately tracked. This may be accomplished via a camera (e.g., visual or ToF) of augmented reality device 30 as known in the art of the present disclosure and/or a surgical navigation system as known in the art of the present disclosure. Additional detection of augmented reality device 30 and the subject anatomy adds may be appropriate for additional accuracy, such as, for example, fiducial marker(s), active marker(s), etc.

Further in practice, visual image sequence controller 40 may interface with a display (not shown), as known in the art of the present disclosure or hereinafter conceived, for displaying an interventional image as commanded by an user-activation of an interactive visual indicator of the present disclosure. Visual image sequence controller 40 may interface with interventional imaging controller 22, as known in the art of the present disclosure or hereinafter conceived, for controlling a re-posing of interventional imaging device 21 as commanded by user-activation of an interactive visual indicator of the present disclosure.

An augmented reality image-guided intervention method of the present disclosure involves, subsequent to or during an acquisition of an interventional imaging sequence by imaging modality 20, augmented reality controller 32 controlling an augmentation of an augmented view of the image-guided intervention via an augment reality display 32 of a visual image sequencing acquisition 42 generated by visual image sequencing controller 40 to include interactive virtual indicators of sequence numbers and imaging directions of the interventional imaging sequence.

For example, FIG. 2 illustrates an exemplary execution of an augmented image-guided intervention method of the present disclosure by the augmented reality image-guided intervention system of FIG. 1.

Referring to FIG. 2, during an image-guided intervention, imaging modality 20 is shown in the form of an X-ray imaging system having a C-arm 21a for acquiring an interventional imaging sequence 23 at different poses of C-arm 21a. For this image-guided intervention example, the X-ray imaging system has acquired of four (4) sequential X-ray images, each at a different pose of C-arm 21a and interventional imaging controller 22 generates a database listing of each X-ray image with corresponding C-arm pose information and an optional annotation by a clinician.

Still referring to FIG. 2, visual image sequence controller 40 accesses an interventional file 41 consisting of the database listing by interventional imaging controller 22 to generate visual imaging sequence acquisition 42a including, for each interventional image of the interventional imaging sequence 23, an interactive virtual indicator of a sequence number and an imaging direction. Augmented reality controller 32 augments an augmented view of the image-guided intervention via an augmented reality display 31a with the visual imaging sequence acquisition 42a of four (4) interactive virtual indicators.

In practice, an interactive virtual indicator may have any form, shape and color to convey a corresponding sequence number and imaging direction. For this example, the interactive virtual indicators are formed as vectors of an arrow shape starting from the center of the projection on the patient and extending outward to the center of the detector position. Next to the end-point of the vector, the sequence number of the interventional image appears.

An interactive virtual indicator may be any virtual indicator with which a user, such as a clinician, is able to interact with; allowing a (two-way) communication or flow of information between a user one or more computers or one or more processors or any device embedding or connected to such computer(s) or processor(s). A clinician may interact with an interactive virtual indicator via using gestures, voice commands or other interactive modes of augmented reality display 31a as known in the art of the present disclosure or hereinafter conceived.

The interventional images of the interventional image sequence 23 are hidden by default, as not to clutter augmented reality display 31a. Only a 'selected' interactive virtual indicator will show a pictorial image 33 corresponding to the 'selected' interactive virtual indicator within a display as known in the art of the present disclosure or hereinafter disclosed (e.g., a display of imaging modality 20, augmented reality display 31 or an additional display monitor).

While the interactive virtual indicators may correspond to interventional images acquired at different poses of C-arm 21a, the image-guided intervention may involve an acquisitions of a temporal series of interventional images at the same pose of C-arm 21a as will be further discussed in the present disclosure. For this embodiment, the interactive virtual indicator may be a vector showing the imaging direction of the C-arm 21a with an associated stack of sequence numbers.

To facilitate an understanding of the present disclosure, the following description of FIGS. 3-16 provides exemplary image-guided intervention in accordance with the present disclosure. From the description of FIGS. 3-16, those having ordinary skill in the art of the present disclosure will appreciate how to apply the present disclosure to any type of image-guided intervention.

Figures 7A, 7B, 7C:
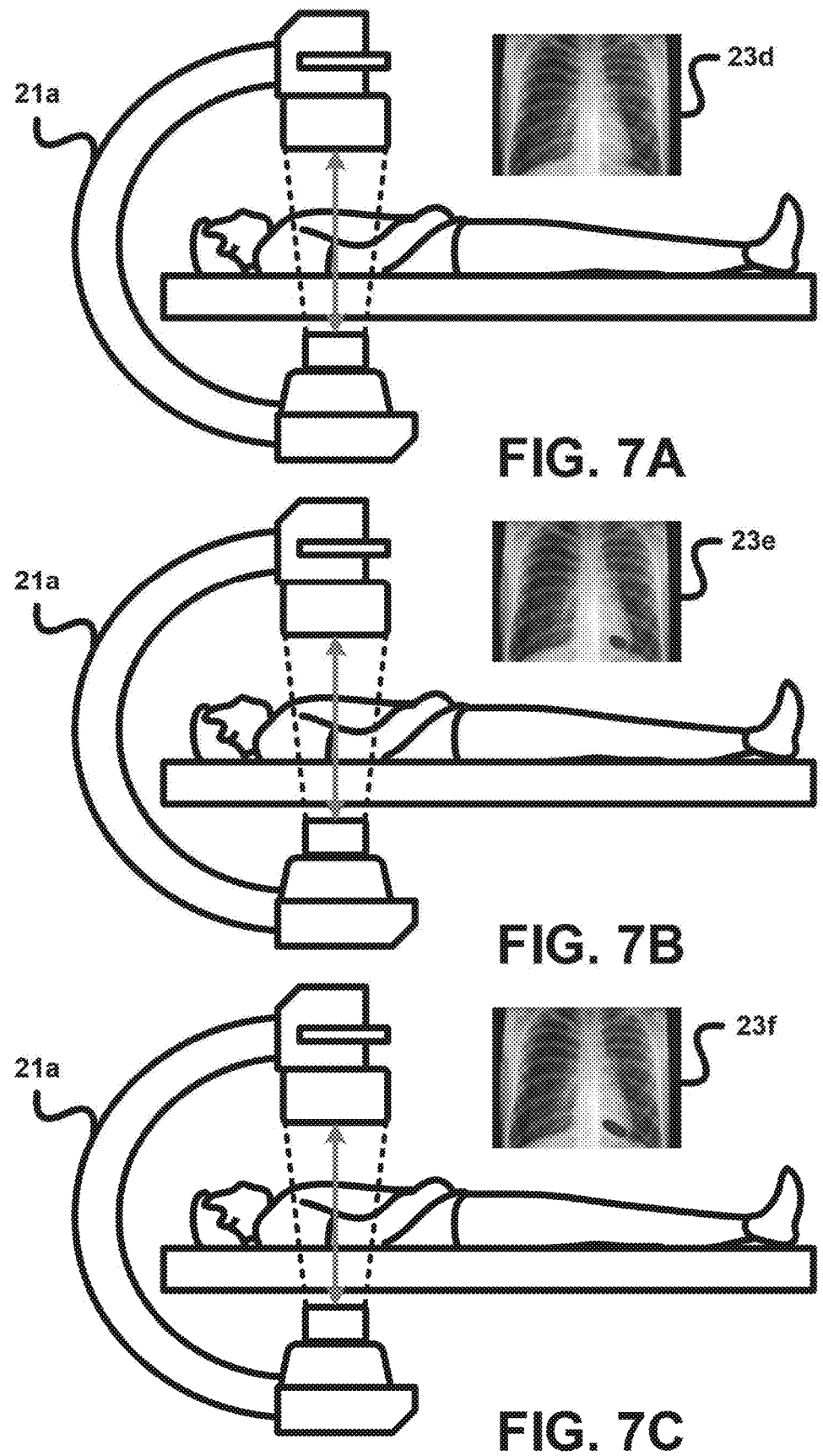
FIGS. 7A-7C illustrate a second exemplary interventional X-ray imaging in accordance with the present disclosure.
Figures 8, 9:
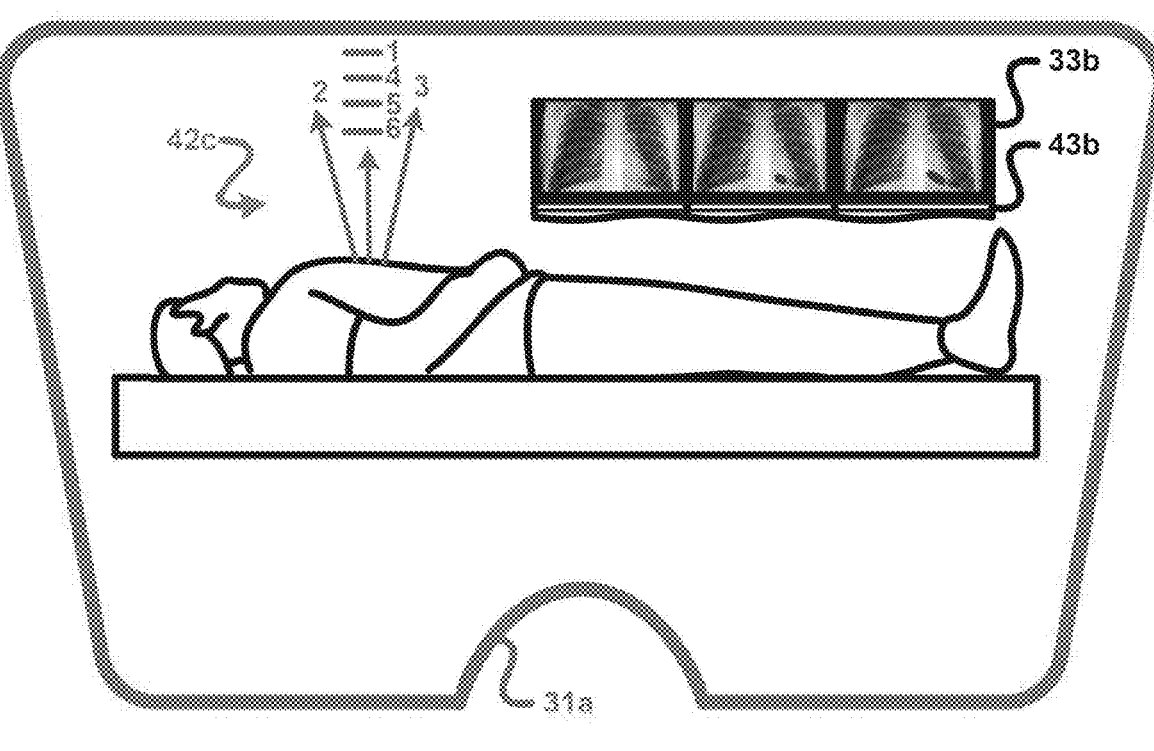
FIG. 8 illustrates an augmented reality of the interventional X-ray imaging of FIGS. 7A-7C in accordance with the present disclosure.
FIG. 9 illustrates an X-ray image display of the interventional X-ray imaging of FIGS. 7A-7C in accordance with the present disclosure.

The first exemplary image-guided intervention involves a diagnosis X-ray imaging phase as shown in FIGS. 3-6 and a treatment X-ray imaging phase as shown in FIGS. 7-9.

Figures 3A, 3B, 3C:
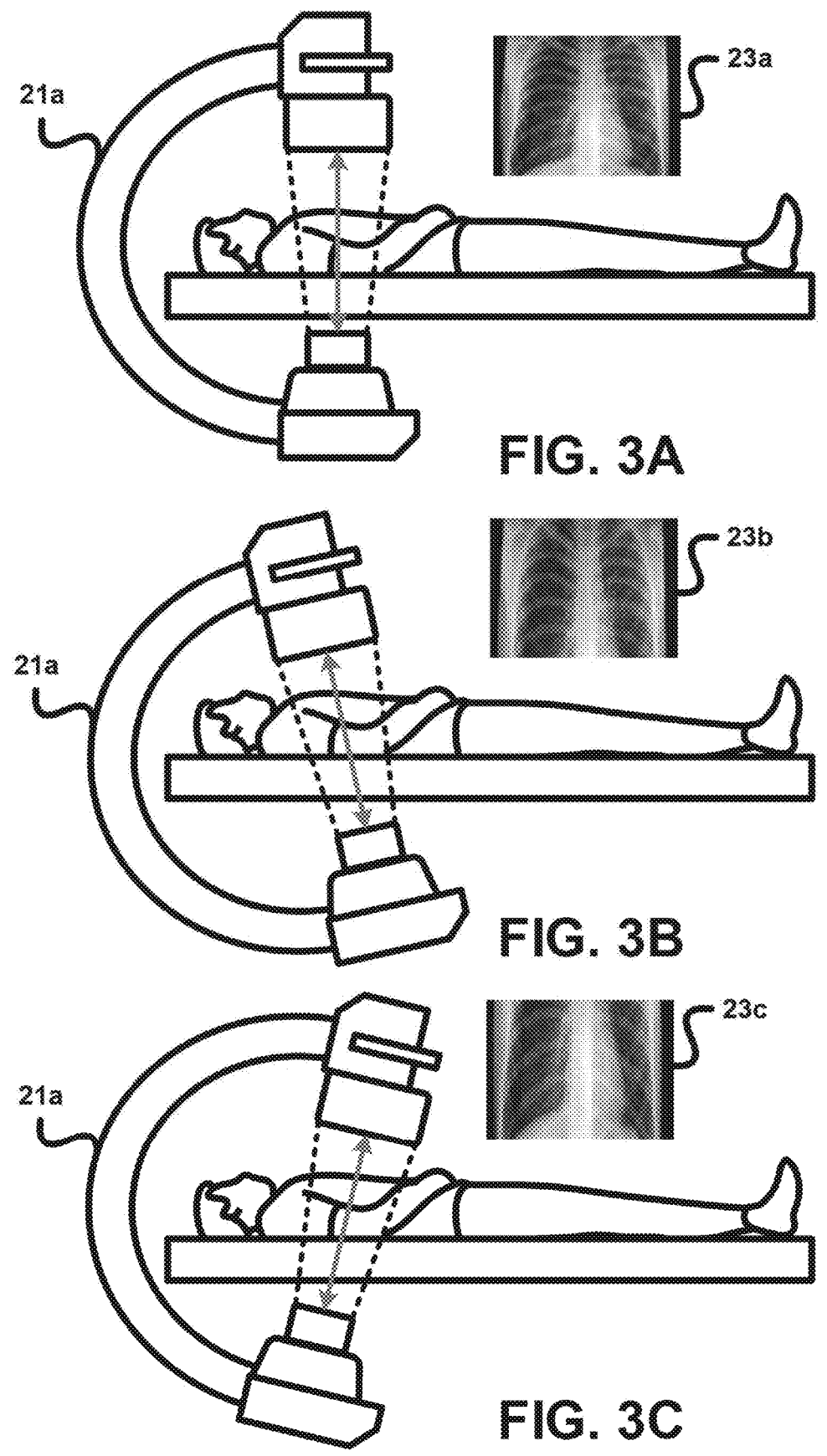
FIGS. 3A-3C illustrate a first exemplary interventional X-ray imaging in accordance with the present disclosure.

More particularly, FIGS. 3A-3C illustrates an acquisition of an interventional imaging sequence of diagnostic X-ray images 23a-23c at different poses of C-arm 21a. FIG. 4 illustrates an augmented view of the diagnostic phase of the image-guided intervention via an augmented reality display 31a including three (3) interactive virtual indicators of a sequence number and image direction of diagnostic X-ray images 23a-23c, respectively. An image 33a corresponding to a selected interactive virtual indicator along with any annotation 43a may also be displayed in augmented reality display 31a and/or the diagnostic X-ray image 23a-23c corresponding to selected interactive virtual indicator may be displayed via a display 24b.

Additionally, if a clinician wishes to return C-arm to a previous pose for purpose of reacquiring a better interventional image at that pose, the clinician may tap the correct interactive virtual indicator or a virtual object C-arm (not shown) and an interventional imaging controller will move the C-arm to the recalled pose. For example, while C-arm 21a is in the pose of FIG. 3C, if the clinician has selected the interactive virtual indicator 1 associated with the C-arm pose of FIG. 3A, the clinician may tap interactive virtual indicator 1 to move the C-arm 21a from the pose of FIG. 3C to the pose of FIG. 3A as exemplary shown in FIG. 6.

FIGS. 7A-7C illustrate a temporal acquisition of an interventional imaging sequence of treatment X-ray images 23d-23f at the same pose of C-arm 21a. FIG. 8 illustrates an augmented view of the treatment phase of the image-guided intervention via an augmented reality display 31a including six (6) interactive virtual indicators of a sequence number and image direction of diagnostic X-ray images 23a-23c and treatment X-ray images 23d-23f, respectively. An images sequence 33b corresponding to a selected interactive virtual indicator of the treatment X-ray images 23d-23f along with any associated annotation 43b may also be displayed in augmented reality display 31a and/or treatment X-ray images 23d-23f corresponding to selected interactive virtual indicator may be displayed via a display 24b.

Figure 14A:
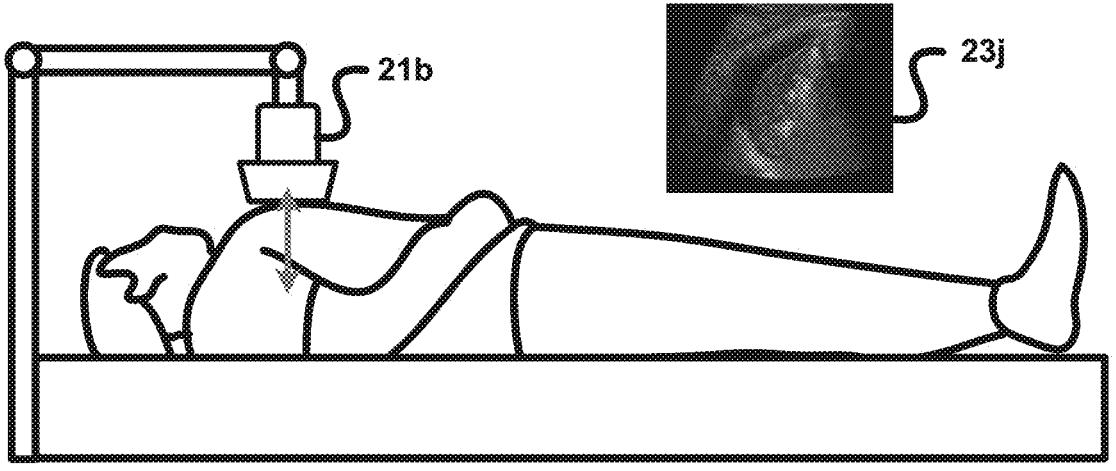
FIGS. 14A-14C illustrate a second exemplary interventional ultrasound imaging in accordance with the present disclosure.
Figure 14B:
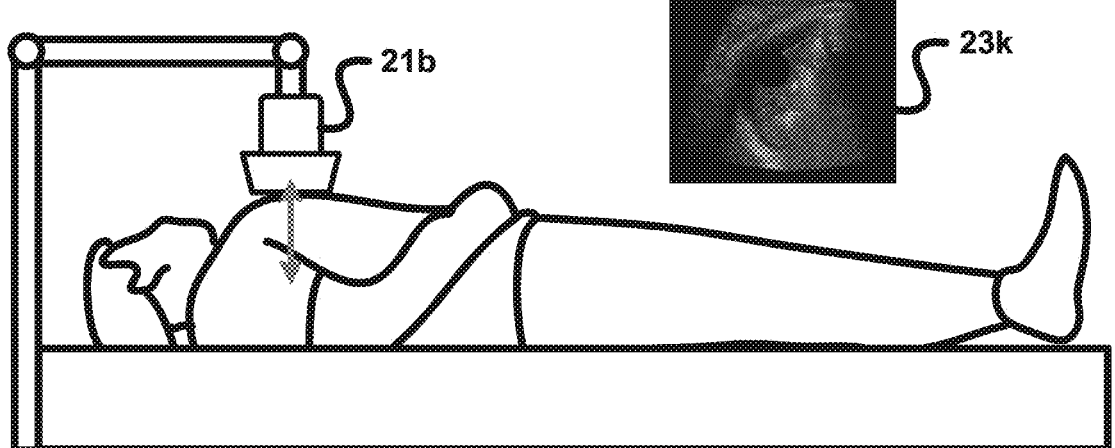
Figure 14C:
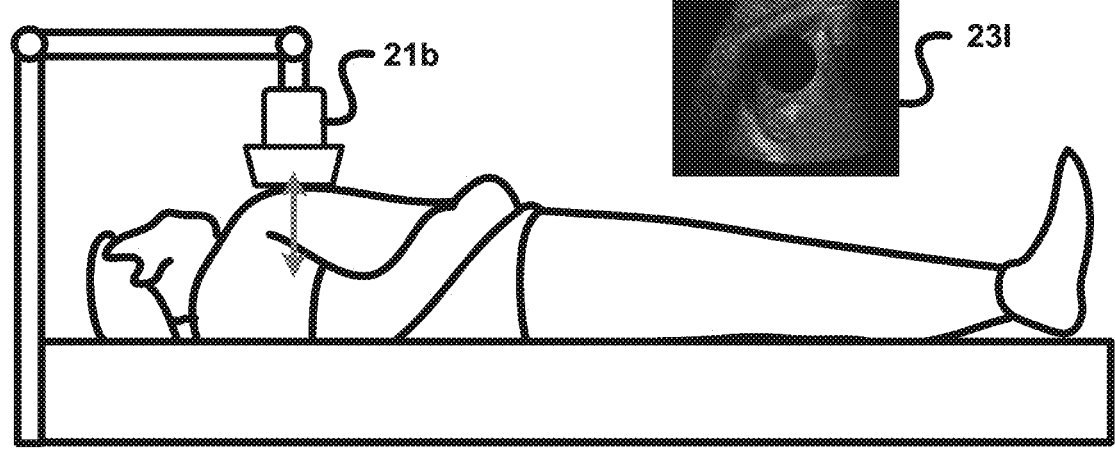
Figure 15:
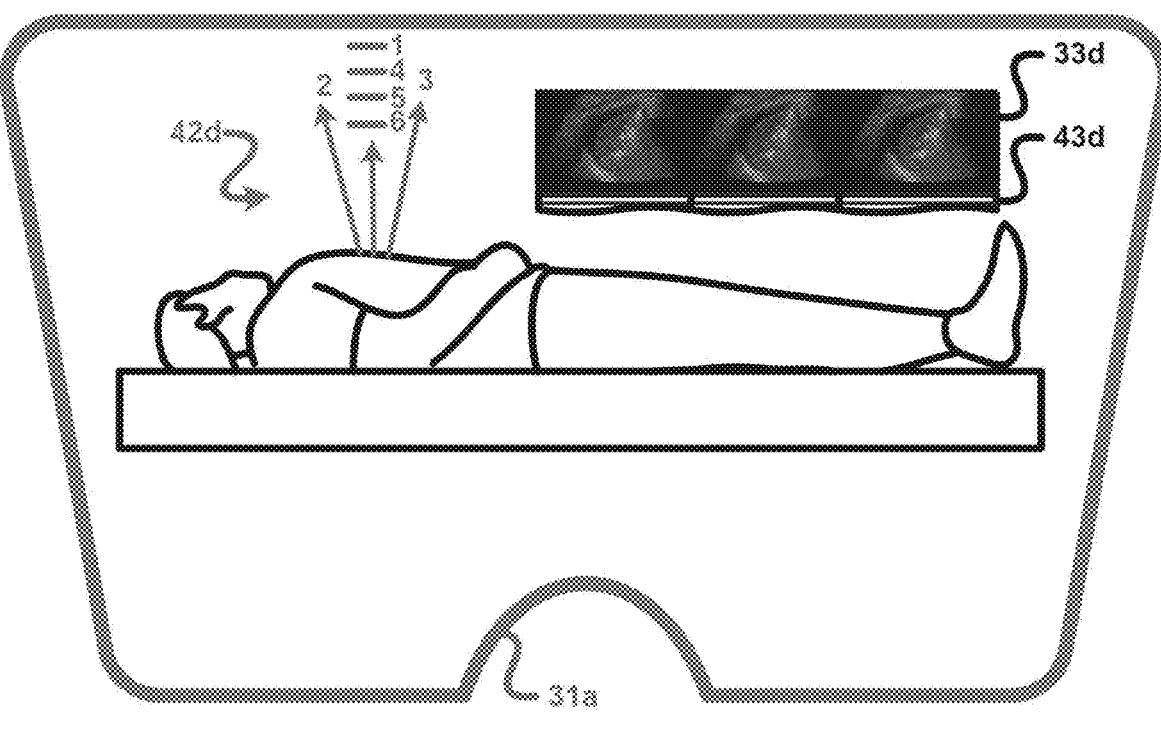
FIG. 15 illustrates an augmented reality of the interventional ultrasound imaging of FIGS. 14A-14C in accordance with the present disclosure.
Figure 16:
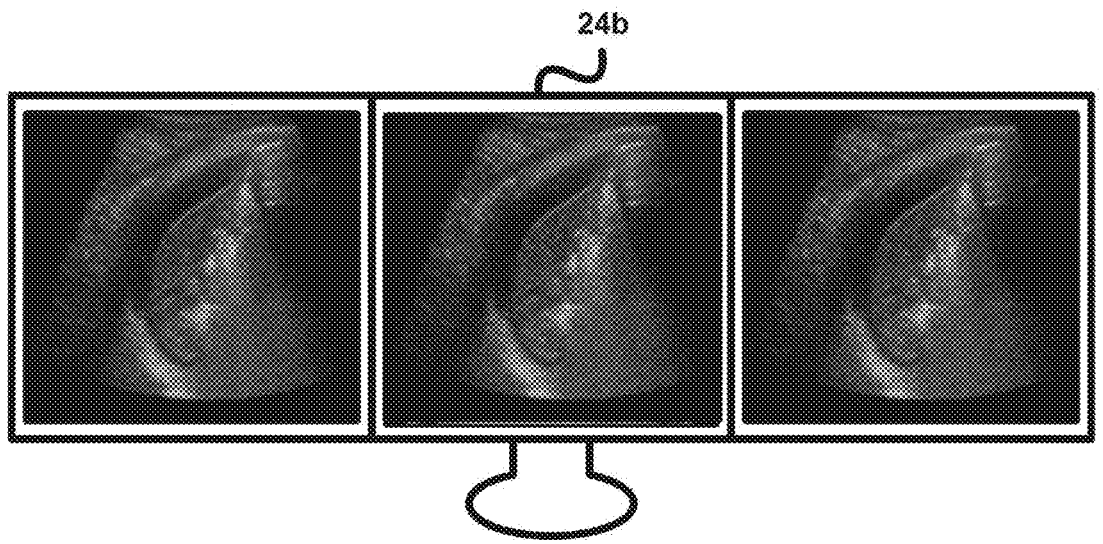
FIG. 16 illustrates an ultrasound image display of the interventional ultrasound imaging of FIGS. 14A-14C in accordance with the present disclosure.

The second exemplary image-guided intervention involves a diagnosis ultrasound imaging phase as shown in FIGS. 10-13 and a treatment ultrasound imaging phase as shown in FIGS. 14-16.

Figure 10A:
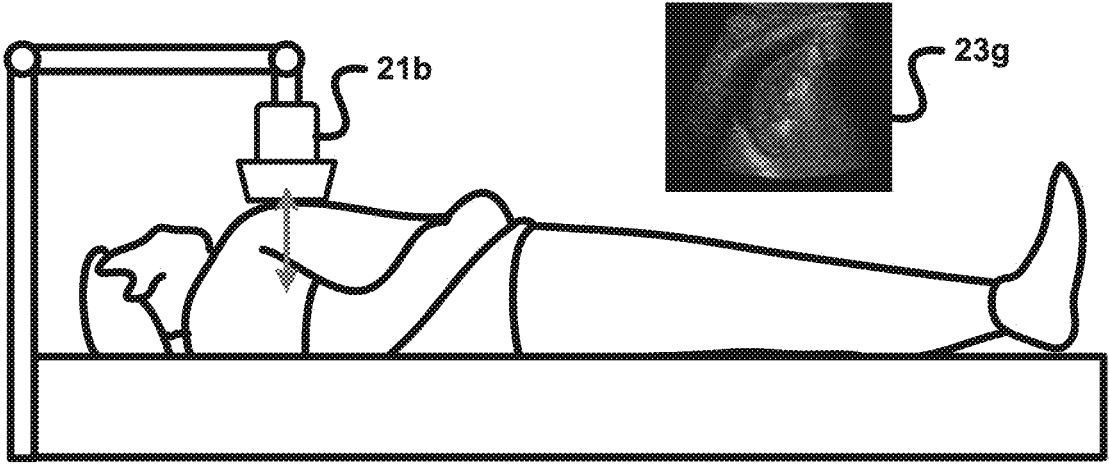
FIGS. 10A-10C illustrate a first exemplary interventional ultrasound imaging in accordance with the present disclosure.
Figure 10B:
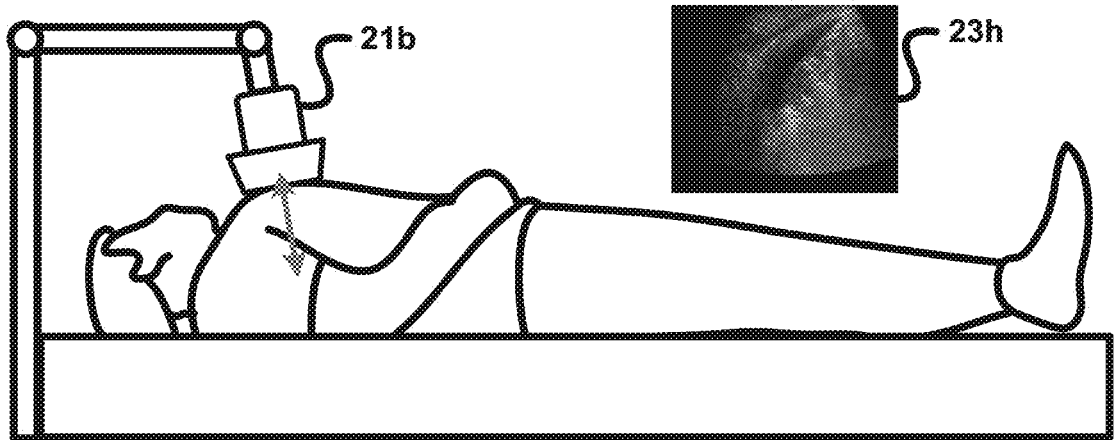
Figure 10C:
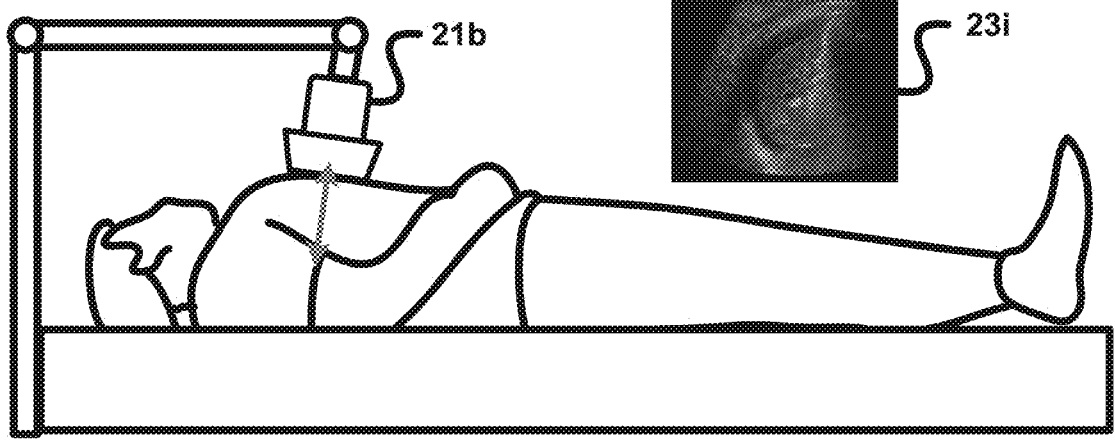

More particularly, FIGS. 10A-10C illustrates an acquisition of an interventional imaging sequence of diagnostic ultrasound images 23g-23i at different poses of robotic ultrasound probe 21b. FIG. 11 illustrates an augmented view of the diagnostic phase of the image-guided intervention via an augmented reality display 31a including three (3) interactive virtual indicators of a sequence number and image direction of diagnostic ultrasound images 23g-23i, respectively. An image 33c corresponding to a selected interactive virtual indicator along with any annotation 43c may also be displayed in augmented reality display 31a and/or the diagnostic ultrasound image 23g-23i corresponding to selected interactive virtual indicator may be displayed via a display 24c.

Additionally, if a clinician wishes to return robotic ultrasound probe to a previous pose for purpose of reacquiring a better interventional image at that pose, the clinician may tap the correct interactive virtual indicator or a virtual object robotic ultrasound probe (not shown) and an interventional imaging controller will move the robotic ultrasound probe to the recalled pose. For example, while robotic ultrasound probe 21b is in the pose of FIG. 10C, if the clinician has selected the interactive virtual indicator 1 associated with the robotic ultrasound probe pose of FIG. 10A, the clinician may tap interactive virtual indicator 1 to move the robotic ultrasound probe 21b from the pose of FIG. 10C to the pose of FIG. 10A as exemplary shown in FIG. 13.

FIGS. 14A-14C illustrate a temporal acquisition of an interventional imaging sequence of treatment ultrasound images 23j-23l at the same pose of robotic ultrasound probe 21b. FIG. 15 illustrates an augmented view of the treatment phase of the image-guided intervention via an augmented reality display 31a including six (6) interactive virtual indicators of a sequence number and image direction of diagnostic ultrasound images 23g-23i and treatment ultrasound images 23j-23l, respectively. An images sequence 33d corresponding to a selected interactive virtual indicator of treatment ultrasound images 23j-23l along with any associated annotation 43d may also be displayed in augmented reality display 31a and/or treatment ultrasound images 23j-23l corresponding to selected interactive virtual indicator may be displayed via a display 24b.

Figures 17A, 17B, 17C:
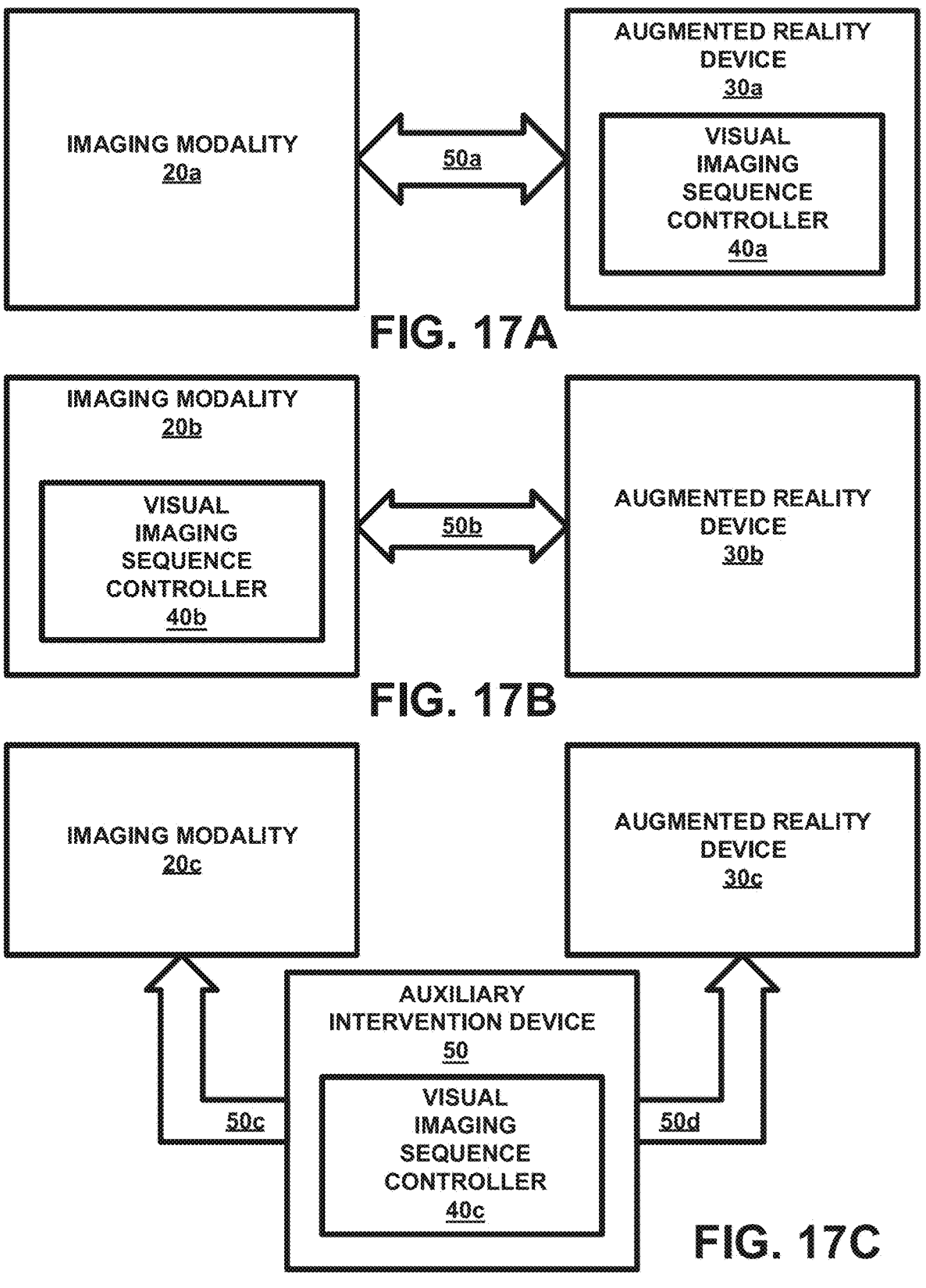
FIGS. 17A-17C illustrate exemplary embodiments of the augmented image-guided intervention system of FIG. 1 in accordance with the present disclosure.

To facilitate a further understanding of the various inventions of the present disclosure, the following description of FIGS. 17A-17C teach exemplary embodiments of an installation of a visual image sequencing controller of the present disclosure in various devices. From this description, those having ordinary skill in the art will appreciate how to apply various aspects of the present disclosure for making and using installation of a visual image sequencing controller of the present disclosure in numerous and various devices of the present disclosure.

Referring to FIG. 17A, a visual imaging sequence controller 40a is in installed within an augmented reality device 30a, whereby communication channel(s) 50a between an imaging modality 20a and augmented reality device 30a facilitates a communication of a linear listing of interventional images from imaging modality 20a to visual imaging sequence controller 40a to thereby support the augmentation of an augmented view of an image-guided intervention as previously described in the present disclosure. This embodiment is suitable for a retrofitting of a visual imaging sequence controller of the present disclosure in augmented reality devices known in the art of the present disclosure or for incorporation of a visual imaging sequence controller of the present disclosure in augmented reality devices hereinafter conceived.

Referring to FIG. 17B, a visual imaging sequence controller 40b is in installed within an imaging modality 20b, whereby communication channel(s) 50b between an imaging modality 20b and augmented reality device 30b facilitates a communication of a visual imaging sequence acquisition of an interventional imaging sequence in a rendered augmented view of the image-guided intervention by the augmented reality device 30b to thereby support the augmentation of an augmented view of an image-guided intervention as previously described in the present disclosure. This embodiment is suitable for a retrofitting of a visual imaging sequence controller of the present disclosure in imaging modalities known in the art of the present disclosure or for incorporation of a visual imaging sequence controller of the present disclosure in imaging modalities hereinafter conceived.

Referring to FIG. 17C, a visual imaging sequence controller 40c is in installed within in an auxiliary intervention device 50, whereby communication channel(s) 50c between auxiliary intervention device 50 and an imaging modality 20c and communication channel(s) 50d between auxiliary intervention device 50 and an augmented reality device 30c facilitates a communication of a linear listing of interventional images from imaging modality 20c to visual imaging sequence controller 40c and a communication of a visual imaging sequence acquisition of an interventional imaging sequence in a rendered augmented view of the image-guided intervention by the augmented reality device 30c to thereby support the augmentation of an augmented view of an image-guided intervention as previously described in the present disclosure. This embodiment is suitable for a non-retrofitting/non-incorporation of a visual imaging sequence controller of the present disclosure in imaging modalities and augmented reality devices known in the art of the present disclosure or hereinafter conceived.

Figure 18:
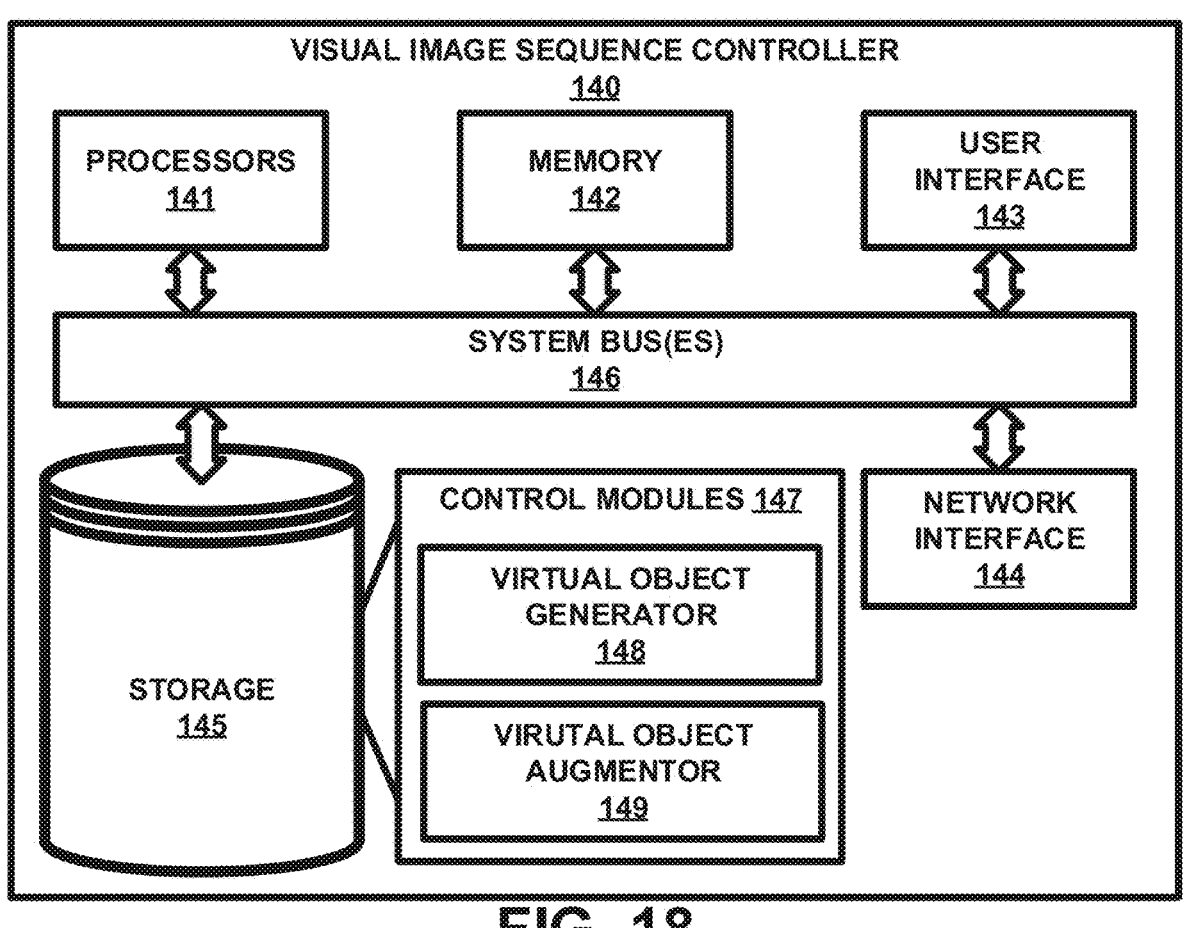
FIG. 18 illustrates an exemplary embodiment of a visual image sequence controller in accordance with the present disclosure.
Figure 19:
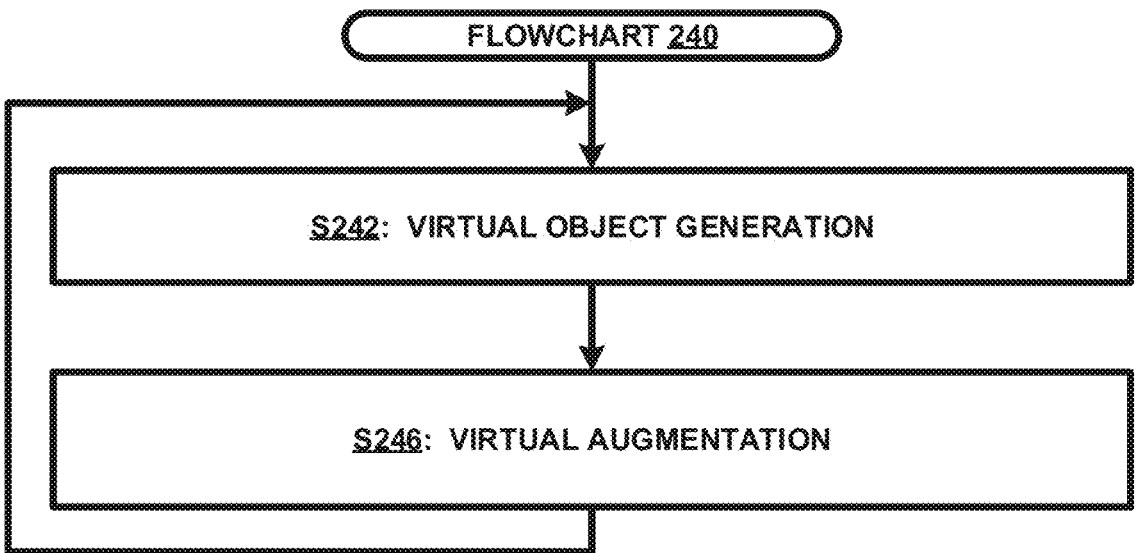
FIG. 19 illustrates an exemplary embodiment of a flowchart representative of a visual image sequencing method in accordance with the present disclosure

To facilitate a further understanding of the various inventions of the present disclosure, the following description of FIGS. 18 and 19 respectively teach an exemplary embodiment of a visual image sequence controller of the present disclosure and an exemplary embodiment of a visual image sequencing method of the present disclosure. From this description, those having ordinary skill in the art will appreciate how to apply various aspects of the present disclosure for making and using additional embodiments of a visual image sequence controller of the present disclosure and a visual image sequencing method of the present disclosure.

Referring to FIG. 18, a visual image sequence controller 140 includes one or more processor(s) 141, memory 142, a user interface 143, a network interface 144, and a storage 145 interconnected via one or more system buses 146.

Each processor 141 may be any hardware device, as known in the art of the present disclosure or hereinafter conceived, capable of executing instructions stored in memory 142 or storage or otherwise processing data. In a non-limiting example, the processor(s) 141 may include a microprocessor, field programmable gate array (FPGA), application-specific integrated circuit (ASIC), or other similar devices.

The memory 142 may include various memories, as known in the art of the present disclosure or hereinafter conceived, including, but not limited to, L1, L2, or L3 cache or system memory. In a non-limiting example, the memory 142 may include static random access memory (SRAM), dynamic RAM (DRAM), flash memory, read only memory (ROM), or other similar memory devices.

The user interface 143 may include one or more devices, as known in the art of the present disclosure or hereinafter conceived, for enabling communication with a user such as an administrator. In a non-limiting example, the user interface may include a command line interface or graphical user interface that may be presented to a remote terminal via the network interface 144.

The network interface 144 may include one or more devices, as known in the art of the present disclosure or hereinafter conceived, for enabling communication with other hardware devices. In a non-limiting example, the network interface 144 may include a network interface card (NIC) configured to communicate according to the Ethernet protocol. Additionally, the network interface 144 may implement a TCP/IP stack for communication according to the TCP/IP protocols. Various alternative or additional hardware or configurations for the network interface 144 will be apparent.

The storage 145 may include one or more machine-readable storage media, as known in the art of the present disclosure or hereinafter conceived, including, but not limited to, read-only memory (ROM), random-access memory (RAM), magnetic disk storage media, optical storage media, flash-memory devices, or similar storage media. In various non-limiting embodiments, the storage 145 may store instructions for execution by the processor(s) 141 or data upon with the processor(s) 141 may operate. For example, the storage 145 may store a base operating system for controlling various basic operations of the hardware. The storage 145 also stores application modules 147 in the form of executable software/firmware for implementing the various functions of the visual image sequence controller 140 as previously described in the present disclosure including, but not limited to, a virtual object generator 148 and a virtual object augmenter 149 for executing a flowchart 240 representative of a visual imaging sequencing method of the present disclosure as shown in FIG. 19.

Referring to FIG. 19, a stage S242 of flowchart 240 encompasses virtual object generator 148 utilizing a linear listing of interventional images to generate interactive virtual indicators as previously described in the present disclosure, and a stage S244 of flowchart 240 encompasses virtual object augmenter 149 augmenting an augmented view of an image-guided intervention with the generated visual object indicators as previously described in the present disclosure.

Referring to FIGS. 1-19, those having ordinary skill in the art of the present disclosure will appreciate numerous benefits of the present disclosure including, but not limited to, a more intuitive and less restrictive way of selecting interventional images for diagnostic and/or treatment purposes during an image-guided intervention.

Further, as one having ordinary skill in the art will appreciate in view of the teachings provided herein, structures, elements, components, etc. described in the present disclosure/specification and/or depicted in the Figures may be implemented in various combinations of hardware and software, and provide functions which may be combined in a single element or multiple elements. For example, the functions of the various structures, elements, components, etc. shown/illustrated/depicted in the Figures can be provided through the use of dedicated hardware as well as hardware capable of executing software in association with appropriate software for added functionality. When provided by a processor, the functions can be provided by a single dedicated processor, by a single shared processor, or by a plurality of individual processors, some of which can be shared and/or multiplexed. Moreover, explicit use of the term "processor" or "controller" should not be construed to refer exclusively to hardware capable of executing software, and can implicitly include, without limitation, digital signal processor ("DSP") hardware, memory (e.g., read only memory ("ROM") for storing software, random access memory ("RAM"), non-volatile storage, etc.) and virtually any means and/or machine (including hardware, software, firmware, combinations thereof, etc.) which is capable of (and/or configurable) to perform and/or control a process.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (e.g., any elements developed that can perform the same or substantially similar function, regardless of structure). Thus, for example, it will be appreciated by one having ordinary skill in the art in view of the teachings provided herein that any block diagrams presented herein can represent conceptual views of illustrative system components and/or circuitry embodying the principles of the invention. Similarly, one having ordinary skill in the art should appreciate in view of the teachings provided herein that any flow charts, flow diagrams and the like can represent various processes which can be substantially represented in computer readable storage media and so executed by a computer, processor or other device with processing capabilities, whether or not such computer or processor is explicitly shown.

The terms "signal", "data" and "command" as used in the present disclosure broadly encompasses all forms of a detectable physical quantity or impulse (e.g., voltage, current, or magnetic field strength) as understood in the art of the present disclosure and as exemplary described in the present disclosure for transmitting information and/or instructions in support of applying various inventive principles of the present disclosure as subsequently described in the present disclosure. Signal/data/command communication between various components of the present disclosure may involve any communication method as known in the art of the present disclosure including, but not limited to, signal/data/command transmission/reception over any type of wired or wireless datalink and a reading of signal/data/commands uploaded to a computer-usable/computer readable storage medium.

It will be appreciated that the term "comprising" does not exclude other elements or steps and that the indefinite article "a" or "an" does not exclude a plurality. A single processor may fulfil the functions of several items recited in the claims. The mere fact that certain measures are recited in mutually different dependent claims does not indicate that a combination of these measures cannot be used to an advantage. Any reference signs in the claims should not be construed as limiting the scope of the claims.

Although claims have been formulated in this application to particular combinations of features, it should be understood that the scope of the disclosure of the present invention also includes any novel features or any novel combinations of features disclosed herein either explicitly or implicitly or any generalisation thereof, whether or not it relates to the same invention as presently claimed in any claim and whether or not it mitigates any or all of the same technical problems as does the parent invention. The applicants hereby give notice that new claims may be formulated to such features and/or combinations of features during the prosecution of the present application or of any further application derived therefrom.

The invention claimed is:

1. A controller for rendering an augmented view of an image-guided intervention, the controller comprising:

at least one processor configured to:

obtain a sequence of images acquired by an image modality during the image-guided intervention;

access geometric information associated with the acquisition of the sequence of images by the imaging modality during the image-guided intervention;

augment the sequence of images with virtual interactive indicators, wherein for each image of the sequence of images, the at least one processor is configured to:

(i) based on the geometric information, determine an imaging parameter of the imaging modality during acquisition of the image, (ii) generate a first interactive virtual indicator indicating a sequence number of the image within the sequence of images and a second interactive virtual indicator indicating the imaging parameter of the imaging modality during the acquisition of the image, and (iii) augment the image with the first interactive virtual indicator and the second interactive virtual indicator;

provide the augmented sequence of images to an augmented reality device to augment a view of the image-guided intervention; and responsive to a user interaction with at least one of the interactive virtual indicators, adjust the imaging modality to acquire a further image.

2. The controller of claim 1, wherein the at least one processor is further configured to annotate the augmented sequence of images based on the geometric information.

3. The controller of claim 1, wherein the at least one processor is further configured to control display of the augmented sequence of images in the augmented view of the image-guided intervention.

4. The controller of claim 1, wherein, responsive to the user interaction with at least one of the interactive virtual indicators, the at least one processor is further configured to adjust a pose of the imaging modality to acquire the further image.

5. The controller of claim 1, wherein the controller is installable within the augmented reality device.

6. The controller of claim 1, wherein:

the controller is installable within the imaging modality; and the at least one processor is further configured to communicate the augmented sequence of images from the imaging modality to the augmented reality device.

7. The controller of claim 1, wherein:

the controller is installable within an auxiliary intervention device; and the at least one processor is further configured to communicate the augmented sequence of images from the auxiliary intervention device to the augmented reality device.

8. A system for rendering an augmented view of an image-guided intervention, the system comprising:

an augmented reality device configured to render an augmented view of an image-guided intervention; and a controller comprising at least one processor configured to:

obtain a sequence of images acquired by an image modality during the image-guided intervention;

access geometric information associated with the acquisition of the sequence of images by the imaging modality during the image-guided intervention;

augment the sequence of images with virtual interactive indicators, wherein for each image of the sequence of images, the at least one processor is further configured to:

(i) based on the geometric information, determine an imaging parameter of the imaging modality during acquisition of the image, (ii) generate a first interactive virtual indicator indicating a sequence number of the image within the sequence of images and a second interactive virtual indicator indicating the imaging parameter of the imaging modality during the acquisition of the image, and (iii) augment the image with the first interactive virtual indicator and the second interactive virtual indicator;

provide the augmented sequence of images to the augmented reality device to augment a view of the image-guided intervention; and responsive to a user interaction with at least one of the interactive virtual indicators, adjust the imaging modality to acquire a further image.

9. The system of claim 8, wherein the at least one processor is further configured to annotate the augmented sequence of images based on the geometric information.

10. The system of claim 8, wherein the at least one processor is further configured to control display of the augmented sequence of images in the augmented view of the image-guided intervention.

11. The system of claim 8, wherein, responsive to the user interaction with at least one of the interactive virtual indicators, the at least one processor is further configured to adjust a pose of the imaging modality to acquire the further image.

12. The system of claim 8, wherein the augmented reality device comprises the controller.

13. The system of claim 8, wherein:

the controller is installable within the imaging modality; and the at least one processor is further configured to communicate the augmented sequence of images from the imaging modality to the augmented reality device.

14. The system of claim 8, wherein:

the controller is installable within an auxiliary intervention device; and wherein the at least one processor is further configured to communicate the augmented sequence of images from the auxiliary intervention device to the augmented reality device.

15. A method of rendering an augmented view of an image-guided intervention, the method comprising:

obtaining a sequence of images acquired by an image modality during the image-guided intervention;

accessing geometric information associated with the acquisition of the sequence of images by the imaging modality during the image-guided intervention;

augmenting the sequence of images with virtual interactive indicators by, for each image of the sequence of images:

(i) based on the geometric information, determining an imaging parameter of the imaging modality during acquisition of the image, (ii) generating a first interactive virtual indicator indicating a sequence number of the image within the sequence of images and a second interactive virtual indicator indicating the imaging parameter of the imaging modality during the acquisition of the image, and (iii) augmenting the image with the first interactive virtual indicator and the second interactive virtual indicator;

augmented, by an augmented reality device, a view of the
image-guided intervention based on the augmented
sequence of images; and responsive to a user interaction with at least one of the
interactive virtual indicators, adjusting the imaging
modality to acquire a further image.

16. The method of claim 15, further comprising annotating the augmented sequence of images based on the geometric information.

17. The method of claim 15, further comprising controlling display of the augmented sequence of images in the augmented view of the image-guided intervention.

18. The method of claim 15, further comprising, responsive to the user interaction with at least one of the interactive virtual indicators, adjusting a pose of the imaging modality to acquire the further image.

* * * * *